United States Patent [19]

Oda et al.

[11] 4,134,796

[45] Jan. 16, 1979

[54] METHOD OF PURIFYING HEXAFLUOROPROPYLENE OXIDE

[75] Inventors: Yoshio Oda; Keiichi Uchida; Shinsuke Morikawa, all of Yokohama, Japan

[73] Assignee: Asahi Glass Company Ltd., Tokyo, Japan

[21] Appl. No.: 852,497

[22] Filed: Nov. 17, 1977

[51] Int. Cl.$^2$ ............... B01D 3/40; C07D 301/32
[52] U.S. Cl. ............... 203/63; 260/348.36; 260/648 F; 260/652 P; 260/653.3
[58] Field of Search ............... 203/67, 63; 260/348.36, 260/653.3, 652 P, 648 F

[56] References Cited

U.S. PATENT DOCUMENTS

| | | | |
|---|---|---|---|
| 3,101,304 | 8/1963 | Wiist | 203/67 |
| 3,282,801 | 11/1966 | Wiist | 203/63 |
| 3,326,780 | 6/1967 | Wiist | 203/63 |

Primary Examiner—Wilbur L. Bascomb, Jr.
Attorney, Agent, or Firm—Oblon, Fisher, Spivak, McClelland & Maier

[57] ABSTRACT

A process for a separation of hexafluoropropylene oxide from hexafluoropropylene by an extractive distillation in the presence of a normally liquid inert compound such as 1,2-dichloroethane, monochlorobenzene, di-isopropyl ether and 1,1,2-trichloroethane.

5 Claims, 1 Drawing Figure

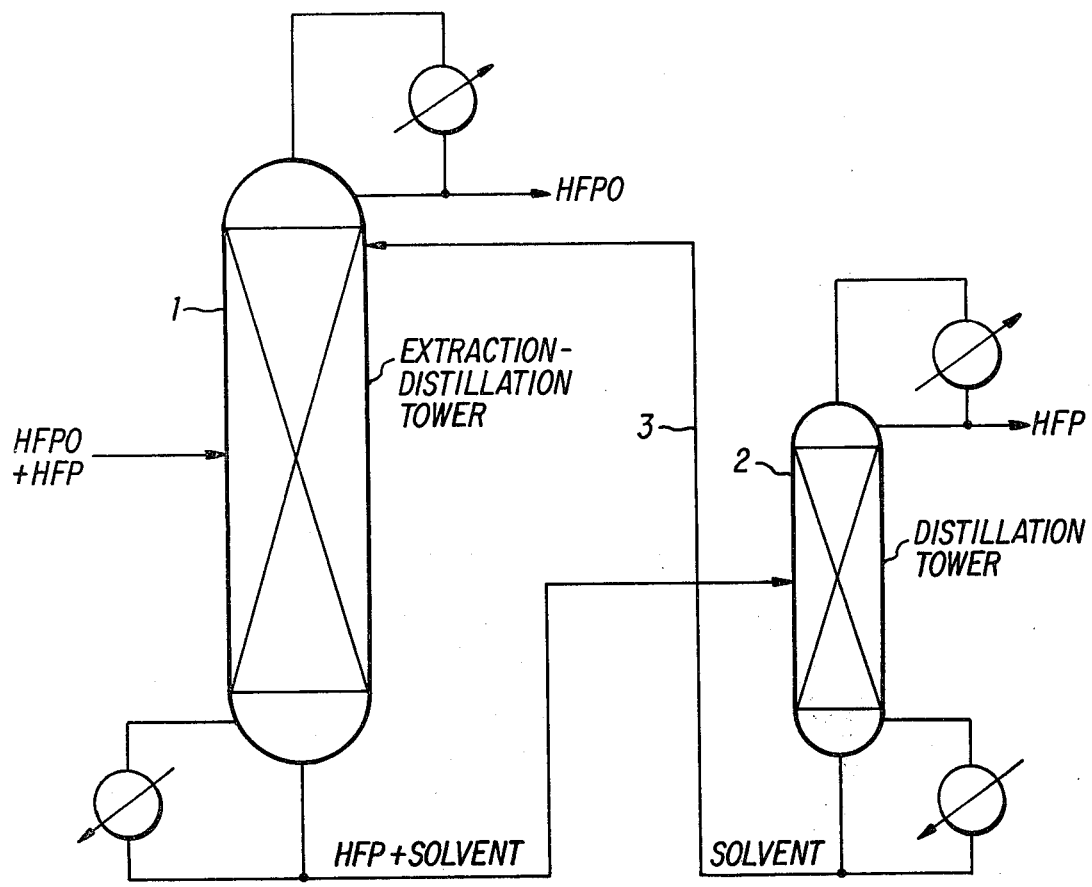

METHOD OF PURIFYING HEXAFLUROPROPYLENE OXIDE

BACKGROUND OF THE INVENTION:

1. Field of the Invention

The present invention relates to a purification of hexafluoropropylene oxide. More particularly, it relates to a separation of hexafluoropropylene oxide from hexafluoropropylene by an extractive distillation.

2. Description of the Prior Art

Hexafluoropropylene oxide (hereinafter referring to as HF PO) can be obtained by an epoxidation of hexafluoropropylene (hereinafter referring to as HFP) in various methods such as the autoxidation and the organic hydroperoxide method.

In these methods, HFPO can be obtained in high selectivity when the reaction condition is adjusted to give a low conversion of HFP. However, the selectivity to HFPO is lowered depending upon an increase of the conversion of HFP. In order to effectively utilize the starting material of HFP, it is preferable that the reaction is stopped under the condition maintaining high selectivity of HFPO and the product is separated from the starting material and the unreacted HFP is recycled to the reaction system.

The crude product obtained by the oxidation contains hexafluoropropylene (HFP) together with several by-products. Some of the by-product may be removed without difficulty by the conventional techniques of scrubbing and distillation, however, the boiling point of HFP is too close to that of HFPO (−29.4° C. and −27.4° C. respectively) to permit the separation by the conventional distillation.

As a method of separating HFP from HFPO, it has been known that HFP is brominated to form the corresponding dibromo compound which has a boiling point being remarkably different from that of HFPO. The dibromo compound is separated by a distillation and then, the dibromo compound is treated with zinc powder and HFP is recovered.

However, the method has disadvantages of a loss of HFP and a necessity for costly processing to remove the reacted material.

In order to overcome the disadvantages, the extractive distillation using a solvent for lowering volatility of HFP to increase the relative volatility of HFPO has been proposed (Japanese Patent Publication No. 14933/1967 and U.S. Pat. No. 3,326,780).

The following solvents has been proposed as suitable solvents in the extractive distillation mono-, di- and tri-substituted benzenes wherein the substituent is an alkyl groups of 1 to 4 carbon atoms, an alkoxyl group of 1 to 4 carbon atoms; dialkyl ethers of ethylene glycol or diethylene glycol wherein the alkyl group of the ether has 1 to 2 carbon atoms; dialkyl carbonates wherein the alkyl group has 1 to 4 carbon atoms; carbon tetrachloride; and chloroform.

SUMMARY OF THE INVENTION

It is an object of the present invention to provide a process for effectively separating hexafluoropropylene oxide from hexafluoropropylene by an extractive distillation.

It is another object of the present invention to provide a solvent for imparting higher separative effect for separating hexafluoropropylene oxide from hexafluoropropylene.

It is the object of the present invention to provide an extractive distillation for separating hexafluoropropylene oxide from hexafluoropropylene with smaller fractionation stages of an extractive distillation tower.

The foregoing and other objects of the present invention can be attained by purifying hexafluoropropylene oxide by separating hexafluoropropylene oxide from hexafluoropropylene by an extractive distillation in the presence of a normally liquid compound selected from the group consisting of chlorinated hydrocarbons having 2 or more carbon atoms and dialkyl ethers wherein at least one alkyl group is branched and has 3 or more carbon atoms.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

The FIGURE is a flow diagram illustrating the method of the invention.

DETAILED DESCRIPTION OF THE PREFERRED EMBODIMENTS

The following problems should be considered in the selection of effective solvents for separating HFPO from HFP by the extractive distillation.

(1) The solvents should be inert to HFP and HFPO.
(2) The solvents should be liquid at lower temperature near the boiling points of HFP and HFPO.
(3) The solvents should not form azeotrope composition with HFP or HFPO.
(4) The solvents should be inexpensive and easily available.

The inventors have studied on solvents depressing a volatility of HFP and increasing a relative volatility of HFPO and have found specific solvents which have the remarkable effect on separation of HFPO from HFP in comparison with the known effective solvents.

That is, the inventors have found that the chlorinated hydrocarbons having 2 or more carbon atoms impart higher efficiency of extractive distillation than carbon tetrachloride or chloroform, and the dialkyl ethers wherein at least one alkyl group is branched and has 3 or more carbon atoms impart higher efficiency of extractive distillation than n-dibutyl ether or ethyleneglycol dimethyl ether. The specific solvents are inert to HFP and HFPO and can be separated from HFP by the conventional distillation.

The present invention has been attained by these findings to provide a process for the separation of HFPO from HFP by an extractive distillation in the presence of a normally liquid compound selected from the group consisting of chlorinated hydrocarbons having 2 or more carbon atoms and dialkyl ethers wherein at least one alkyl group is branched and has 3 or more carbon atoms.

In accordance with the process of the present invention, higher effects of separation can be attained in comparison with those of using the conventional solvents such as chloroform, ethyleneglycol dimethyl ether etc.

That is, as it is clear from the following results of the measurement of relative volatility, the relative volatilities of HFPO to HFP in the presence of the conventional solvents are about 1.3 whereas the relative volatilities of HFPO to HFP in the presence of the specific solvents such as monochlorobenzene or di-isopropyl ether are about 1.4 to 2.0 and that in the presence of 1,2-dichloroethane is about 1.6 to 3.2.

In accordance with the process of the present invention, the numbers of fractionation stages of the extractive distillation tower can be remarkably decreased and the size of the tower can be miniaturized. Accordingly, the process of the present invention attain remarkable advantages in the industrial process.

Suitable solvents used in the process of the present invention include chlorinated hydrocarbons having 2 or more carbon atoms such as propylchlorides, butylchlorides, amylchlorides, 1,1,2-trichloroethane, trichloroethylene, tetrachloroethylene, 1,2-dichloroethane, 1,1-dichloroethane, chlorobenzenes, dichloroethylenes, dichloropropanes, 1,3-dichlorobutane and 1,4-dichlorobutane; dialkyl ethers wherein at least one alkyl group is branched and has 3 or more carbon atoms such as di-isopropyl ether, isopropyl methyl ether, isopropyl ethyl ether, methyl isobutyl ether and ethyl isobutyl ether.

In the process of the present invention, the solvents should be the specific solvent and preferably have the above-mentioned characteristics of (1) to (4). That is, the chlorinated hydrocarbons or ethers which have a solidification point of lower than $-20°$ C. preferably lower than $-40°$ C. and a boiling point of higher than $0°$ C., preferably 20 to $150°$ C. and are liquid under the condition of the extractive distillation may be selected.

The preferred solvents are di-isopropyl ether, chlorobenzenes, 1,2-dichloroethane and 1,1,2-trichloroethane. It is especially preferable to use 1,2-dichloroethane since 1,2-dichloroethane imparts two times or more effect of separation to the conventional effective solvents.

Esters such as methyl benzoate, methyl formate; cyclohexene and dibutyl ether have the above-mentioned characteristics of (1) to (4), however they have not the effect for improving the relative volatility of HFPO to HFP.

The solvent may be present in a weight ratio of HFPO of from about 0.2:1 to 1000:1 and preferably from about 1:1 to 10:1.

The optimum operating conditions will depend upon the desired purity of HFPO and the effective number of fractionation stages in a given column.

The extractive distillation is carried out under higher than the atmospheric pressure preferably 1 to 10 atoms. The temperature in the distillation is varied depending upon variation of the pressure. For example, the temperature at the top of the tower is in a range of $-30°$ C. to $+50°$ C.

The selection of the solvents as the eluents is attained by measuring the relative volatility of HFPO to HFP by using the Othmer type pressure equilibrium distillation apparatus.

The solvent, HFPO and HFP are charged in the pressure equilibrium distillation apparatus at desired ratios and the apparatus is heated to reflux for 3 to 6 hours under the pressure of 2 to 3.5 $Kg/cm^2$ at the temperature of 7 to $12°$ C. at the top and 15 to $28°$ C. in the apparatus.

Then, the condensed liquid of the vapor phase and the liquid of the liquid phase in the apparatus are respectively sampled and the mole ratios of HFPO to HFP in the liquids are respectively measured by a gas-chromatography. The relative volatility is calculated from the results of the measurement. The method of the invention is illustrated in the Figure. A mixture of HFPO (50%) and HFP (50%) was continuously fed to tower (1) and a solvent was continuously fed through line (3) to carry out an extraction-distillation. HFPO having a purity of 99.6% was obtained from the top of the tower and a mixture of HFP and the solvent containing 3% of HFPO was obtained from the bottom. The resulting mixture is fed into tower (2) to carry out a distillation and HFP having a purity of 97% was recovered. The solvent obtained from the bottom was recycled through line (3).

The following examples are presented to illustrate and not to restrict the present invention. Percentages are by mole unless otherwise noted.

EXAMPLE 1

In the Othmer type pressure equilibrium distillation apparatus, the vapor-liquid equilibrium of HFPO and HFP in the presence of 1,2-dichloroethane was measured in the range of 0.2 to 0.9 mole fraction of HFPO in the liquid phase and the relative volatility was calculated by Fenske's equation to give 1.6 to 3.3. In the distillation tower having 20 fractionation stages, a mixture of 50% of HFPO and 50% HFP was continuously fed at a rate of 150 g per hour and 1,2-dichloroethane was fed from the top of the tower at a rate of 300 g per hour and the extractive distillation was carried out under controlling a reflux of 2.5. In the distillation, the pressure in the system was 2.1 $Kg/cm^2G$ and the temperature was $8°$ C. at the top and $17°$ C. at the bottom.

The products were samples from the top and the bottom, and analyzed to find 99.6% of HFPO at the top and 97% of HFP at the bottom. When the conventional effective solvent such as ethyleneglycol dimethyl ether was used, the relative volatility was 1.3. Accordingly, the fractionation stages needed for the distillation under the same condition are 54 fractionation stages.

EXAMPLE 2

In the Othmer type pressure equilibrium distillation apparatus, the vapor-liquid equilibrium of HFPO and HFP in the presence of diisopropyl ether was measured and the relative volatility was calculated by Fenske's equation to give 1.42. In the distillation tower having 41 fractionation stages, a mixture of 50% of HFPO and 50% of HFP was continuously fed at a ratio of 150 g per hour and di-isopropyl ether was fed from the top of the tower at a rate of 215 g per hour and the extractive distillation was carried out under controlling a reflux ratio of 7.1 In the distillation, the pressure in the system was 2.2 $Kg/cm^2$ G and the temperature was $11°$ C. at the top and $28°$ C. at the bottom.

The products were sampled from the top and the bottom, and analyzed to find 99.6% of HFPO at the top and 3% of HFPO at the bottom.

EXAMPLE 3

In the Othmer type pressure equilibrium distillation apparatus, the vapor-liquid equilibrium of HFPO ad HFP in the presence of monochlorobenzene was measured and the relative volatility was calculated to give 1.75. The number of fractionation stages in the distillation tower needed for obtaining 99.6% of HFPO at the top and 97% of HFP at the bottom, was calculated from the Gilliland's relative relationship, to give 26 fractionation stages.

When the conventional effective solvent of ethyleneglycol dimethyl ether was used, the relative volatility was 1.3. Accordingly, the fractionation stages needed for the distillation under the same condition are 54 fractionation stages.

EXAMPLE 4

In accordance with the process of Example 2 except using 1,1,2-trichloroethane instead of di-isopropyl ether, the relative volatility of HFPO and HFP was measured to give 1.80.

EXAMPLE 5

In accordance with the process of Example 2 except using trichloroethylene instead of di-isopropyl ether, the relative volatility of HFPO ad HFP was measured to give 1.75.

What is claimed is:

1. A method of purifying hexafluoropropylene oxide which comprises separating hexafluoropropylene oxide from hexafluoropropylene by an extractive distillation in the presence of a normally liquid compound selected from the group consisting of chlorinated hydrocarbons having 2 or more carbon atoms and dialkyl ethers wherein at least one alkyl group is branched and has 3 or more carbon atoms, and recovering purified hexafluoropropylene oxide as the distillate.

2. The method of claim 1 wherein the normally liquid compound is 1,2-dichloroethane.

3. The method of claim 1 wherein the normally liquid compound is monochlorobenzene.

4. The method of claim 1 wherein the normally liquid compound is di-isopropyl ether.

5. The method of claim 1 wherein the normally liquid compound is 1,1,2-trichloroethane.

* * * * *